United States Patent [19]

Berger et al.

[11] Patent Number: 4,865,580
[45] Date of Patent: Sep. 12, 1989

[54] INFLATION SYSTEM, IN PARTICULAR FOR CARDIAC ASSISTANCE

[75] Inventors: Henri Berger, Paris; René Veragen, Chatou, both of France

[73] Assignee: Societe d'Applications Generales d'Electricite et de Mechanique SAGEM, Paris, France

[21] Appl. No.: 137,937

[22] Filed: Dec. 28, 1987

[30] Foreign Application Priority Data

Dec. 30, 1986 [FR] France ............................. 86 18332

[51] Int. Cl.⁴ .......................................... A61B 19/00
[52] U.S. Cl. .................................... 600/18; 417/315; 623/3
[58] Field of Search ............... 128/1 D, 683; 417/315; 623/3; 600/16, 17, 18

[56] References Cited

U.S. PATENT DOCUMENTS 3,783,453 1/1974 Bolie ..................................... 128/1 D
4,116,589 9/1978 Rishton .............................. 128/1 D
4,381,567 5/1983 Robinson et al. .................. 128/1 D
4,718,833 1/1988 Berger ..................................... 623/3

FOREIGN PATENT DOCUMENTS 2558921 7/1977 Fed. Rep. of Germany .
2580339 10/1986 France .

Primary Examiner—Max Hindenburg
Assistant Examiner—J. P. Lacyk
Attorney, Agent, or Firm—Stevens, Davis, Miller & Mosher

[57] ABSTRACT

An inflation system, in particular for cardiac assistance, has a rotary distributor driven by a motor controlled by an electronic circuit. The rotary distributor places a bag and an inflation fluid reservoir in communication through a pump for alternately inflating the bag from the reservoir and emptying the bag into the reservoir. The electronic circuit controls the rotary distributor during inflation and deflation and progressively controls the speed of the pump during inflation, and during deflation interrupts the power supply to the motor.

14 Claims, 3 Drawing Sheets

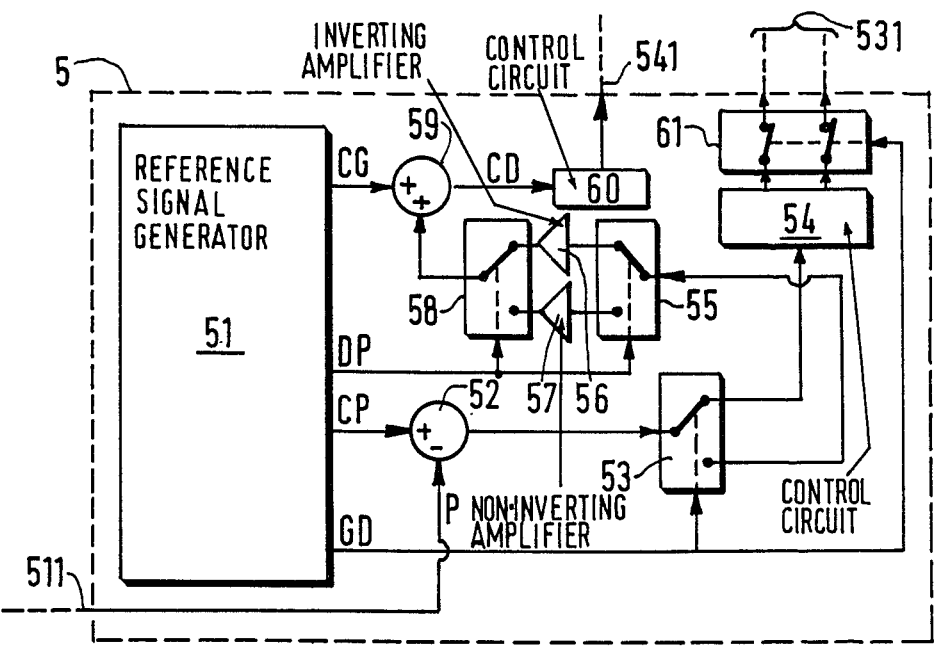
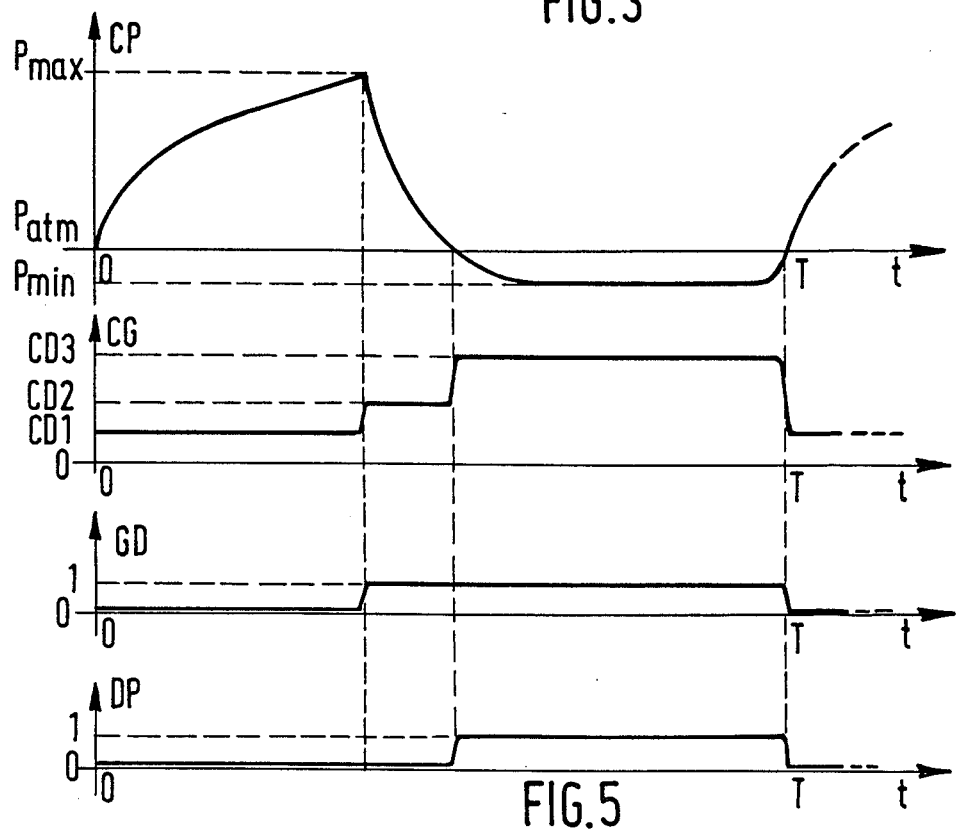

INFLATION SYSTEM, IN PARTICULAR FOR CARDIAC ASSISTANCE

BACKGROUND OF THE INVENTION

1. Field of the Invention

The present invention relates to a system for inflating and deflating at least one bag, including a reservoir of an inflation fluid, at least one pump with an inlet and an outlet, means for driving the pump, means for supplying the driving means with power, means for placing the bag, the reservoir, the pump inlet and the pump outlet in communication and means for controlling the power supply means and the communication means so as to alternately inflate and deflate the bag, in which system the control means and the means providing communication are arranged so that, during inflation, the reservoir communicates with the inlet of the pump and the bag communicates with the outlet of the pump, the power supply means being in service and so that, during deflation, the reservoir communicates with the bag, the power supply means being switched off.

Such a system is used in the biomedical field, for example, and in particular for cardiac assistance, that is to say the control of a cardiac module or artificial heart. An artificial heart is formed essentially of two ventricles, each having a flexible bag containing blood, the deformation of which for aspirating and delivering this blood is controlled by the deformation of another flexible bag alternately inflated then deflated by means of a system similar to the above system, with an inflation fluid such as air or nitrogen. Such a system may also be used in an artificial breathing apparatus.

2. Description of the Prior Art

A system of the above defined type is already known from the patent application filed in the German Federal Republic No. 2 558 921

In this system, because the reservoir communicates directly with the bag, during deflation, it is necessary, so that the bag is completely emptied into the reservoir, for the latter to be able to produce a suction effect itself, which effect is obtained through the deformability of the reservoir and the spring with which it is provided. Such a characteristic however complicates the construction and use of the system. In addition, during deflation, the bag is placed suddenly in communication with the reservoir, which results in a sharp variation of the pressure of the fluid which it contains which may be prejudicial to the correct operation of the cardiac module, and rapidly fatigue the components thereof.

A system is also known, from French application No. 2 580 339 for a cardiac module of closely related type, intended to be implanted in the body of the patient. In this system, the inflation fluid is air or nitrogen from an implanted reservoir and, for inflating and deflating the two bags, a single gear pump is used whose two gears are permanently driven at high speed, as well as two distributors controlled so as to place each of the bags progressively in communication with the inlet or outlet of the pump. In this system, discontinuities may however occur, as in the preceding system, in the pressure variation of the fluid in the bag. In fact, since each distributor is controlled by means of a stepper motor controlling the useful section of the communication orifice between the bag and the inlet or outlet of the pump, the variations in section of this orifice are quantified and it may happen that for the lowest non zero value of this section, the suction, or the delivery produced by the pump in the bag remains too strong, because the latter is permanently driven at high speed. In addition, the permanent driving of the pump leads to a relatively high electric energy consumption, which is obviously a drawback in the case of a device implanted in a patient, fed for example by a battery which is also implanted.

SUMMARY OF THE INVENTION

The present invention overcomes the above drawbacks. For this, it provides a system of the above defined type, characterized by the fact that said control means and said communication means are adapted for, during inflation, controlling the means driving the pump and causing the pressure of the fluid in the bag to evolve so that at all times it is equal to a reference pressure in accordance with a predetermined law and, during deflation, placing the bag in communication with the inlet of the pump and the reservoir with the outlet of the pump.

With the system of the invention, control of the means driving the pump so as to cause the pressure of the fluid in the bag to evolve always results in a continuous variation of this pressure, because of the "smoothing" phenomenon related to the inertia of the pump and its drive means. Thus the predetermined law which, in a cardiac module for example, is a law chosen by the doctor so as to simulate as well as possible the operation of a real heart, or else because it is better suited to the patient, is followed without discontinuities. Because of this same inertia of the pump and its drive means, during deflation and despite switching off of the electric supply means, the pump continues to operate, certainly at a speed decreasing in time, but which remains sufficient to allow the bag to be emptied into the reservoir for, because the pressure in the bag is higher than the pressure in the reservoir after inflation, the bag tends to empty naturally therein to. In addition, with the speed of the pump being relatively low at the end of the deflation phase, there is practically no discontinuity at the time of deflation-inflation transition, nor in the following instants, because the rising speed of the pump cannot be instantaneous. Finally, the fact of switching off the power supply means during deflation makes it possible to reduce considerably the energy consumption, which is, as was mentioned, an important advantage in the case of possible implantation of the system in a patient.

In this invention, it is remarkable that the preceding results were attained more particularly by placing the bag in communication, during deflation, with the inlet of the pump and the reservoir with the outlet of the pump, so as to use the mechanical energy stored in the pump because of its inertia, so as to completely empty the bag into the reservoir.

Such a characteristic is remarkable for it is apparent, from reading the German application No. 2 558 921 already mentioned, that although, in the system which is described therein, the power supply for the motor of the pump is cut off during deflation, it is because the pump, only able to transfer the fluid from the reservoir to the bag, can only oppose complete deflation of the bag. To optimize the operation of this system, a man skilled in the art would then have the idea of attempting to completely immobilize the motor during deflation. This idea is opposite the one put into practice in the present invention, namely the use of the energy stored by inertia in the motor, both for saving electric energy and for attenuating the pressure variations to which the cardiac module is subjected.

In accordance with the first characteristic of the present invention, with the communication means being adapted so as to place the reservoir and the bag progressively in communication through the pump so as to empty the bag into the reservoir, said control means are adapted for controlling the communication means during deflation and causing the pressure of the fluid in the bag to evolve so that it is equal at all times to a reference pressure in accordance with a predetermined law.

Thus, during deflation and despite the absence of control of the pump, a predetermined law can be imposed for the pressure in the bag, because of the possibility of adjustment provided by the progressive control of the communication establishing means.

According to another feature of the present invention, with the communication establishing means adapted for placing the reservoir and the bag directly in communication, said control means are adapted for controlling the communication establishing means during deflation so that the bag begins by emptying itself directly into the reservoir then the pump continues to empty the bag into the reservoir.

In fact, as long as the pressure in the bag is greater than the pressure in the reservoir, which is the case at the beginning of deflation, it is pointless to use the pump for emptying the bag into the reservoir.

Advantageously, a sensor is provided for measuring the pressure in the bag, said control means being connected to the sensor and adapted for comparing the pressure measured by the sensor with said reference pressure and progressively controlling the drive means during inflation and the communication establishing means during deflation.

BRIEF DESCRIPTION OF THE DRAWINGS

The present invention will be better understood from the following description of a preferred embodiment of the system of the invention, with reference to the accompanying drawings in which:

FIG. 3 shows a block diagram of the electronic circuit of the system of FIG. 1, FIG. 5 shows a timing diagram of the different signals of the electronic circuit of FIG. 3.

MORE DETAILED DESCRIPTION OF THE INVENTION

Figure 1:
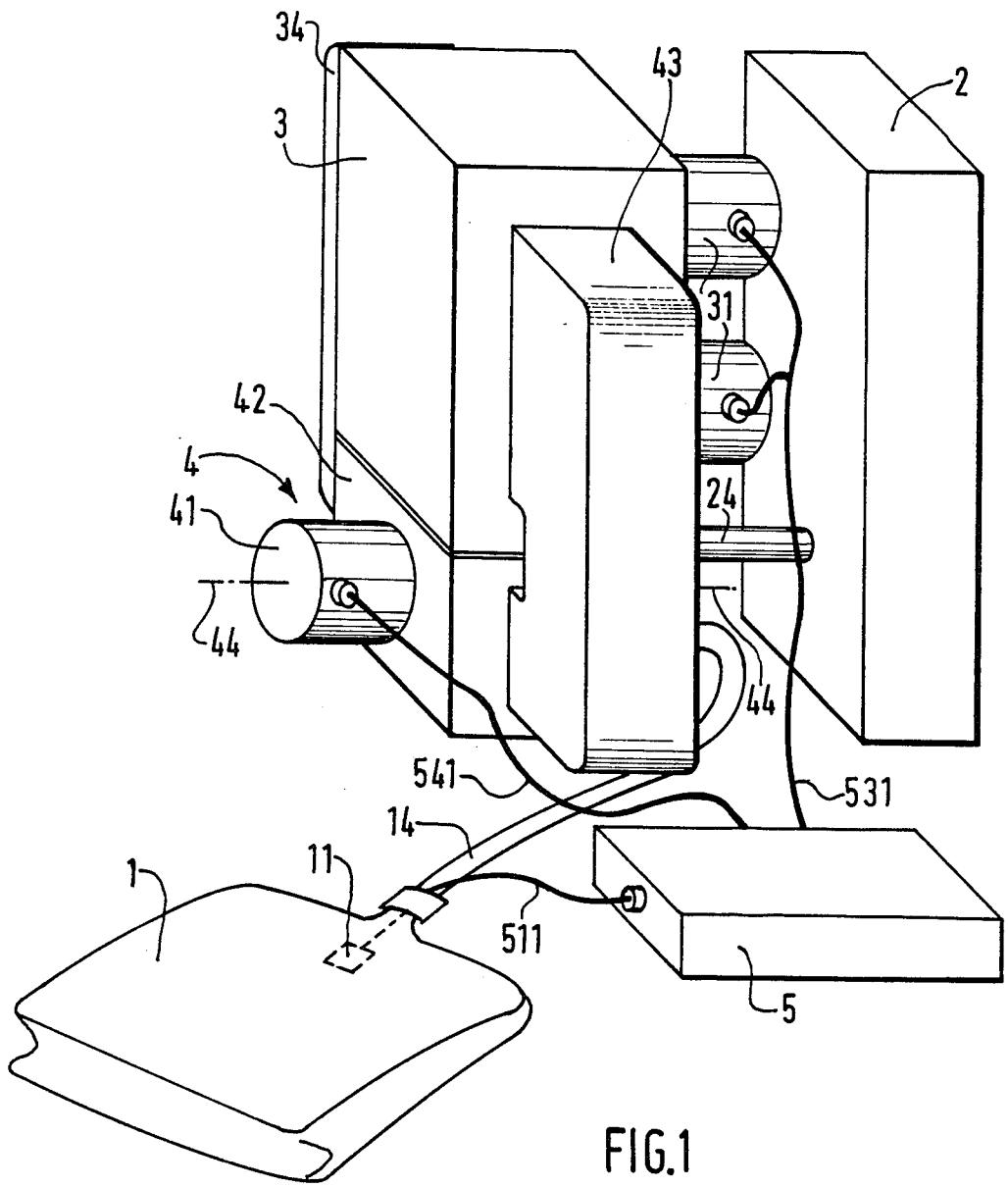
FIG. 1 shows a schematical perspective view of the system of the invention, and a bag to be inflated and deflated.

In FIG. 1 is shown a system for inflating and deflating a flexible bag 1 intended here for an artificial heart. In a way known per se, an artificial heart is formed of two ventricles, each comprising a flexible bag containing blood. The deformation of each blood bag for sucking up or delivering the blood is controlled by the deformation of a bag similar to the bag in FIG. 1, alternately inflated and deflated with, here, air.

For the sake of simplicity, although it requires two air bags for controlling the two ventricles of an artificial heart, only a single air bag 1 has been shown in FIG. 1.

As shown in this FIG., bag 1 communicates with the body 42 of a distributor, here rotary, through a duct 14. The body 42 of distributor 4 also communicates with an air reservoir 2 through a duct 24. A pump 3, here of known type with two toothed gear wheels, each wheel which is driven by a motor 31, is provided with an inlet and an outlet which communicate with the body 42 of distributor 4 through a duct 34 and through a duct 43, respectively.

As will be described in greater detail hereafter, the distributor 4 includes a motor 41, with axis 44, which controls the position of a rotary piece in body 42, so as to place in communication:

either simultaneously, the inlet of pump 3 with reservoir 2 and the outlet of pump 3 with bag 1, so as to inflate bag 1 from reservoir 2, or simultaneously the inlet of pump 3 with bag 1 and the outlet of pump 3 with reservoir 2, so as to empty bag 1 into reservoir 2, or else the inlet of pump 3 with its outlet, with the reservoir 2 and with bag 1 so in particular that bag 1 empties itself alone into reservoir 2.

Bag 1 is provided with a pressure sensor 11.

An electronic circuit 5 is connected to sensor 11, to the motor 41 of distributor 4 and to the motors 31 of pump 3 through connections 511, 541 and 531 respectively.

Figures 2, 4:
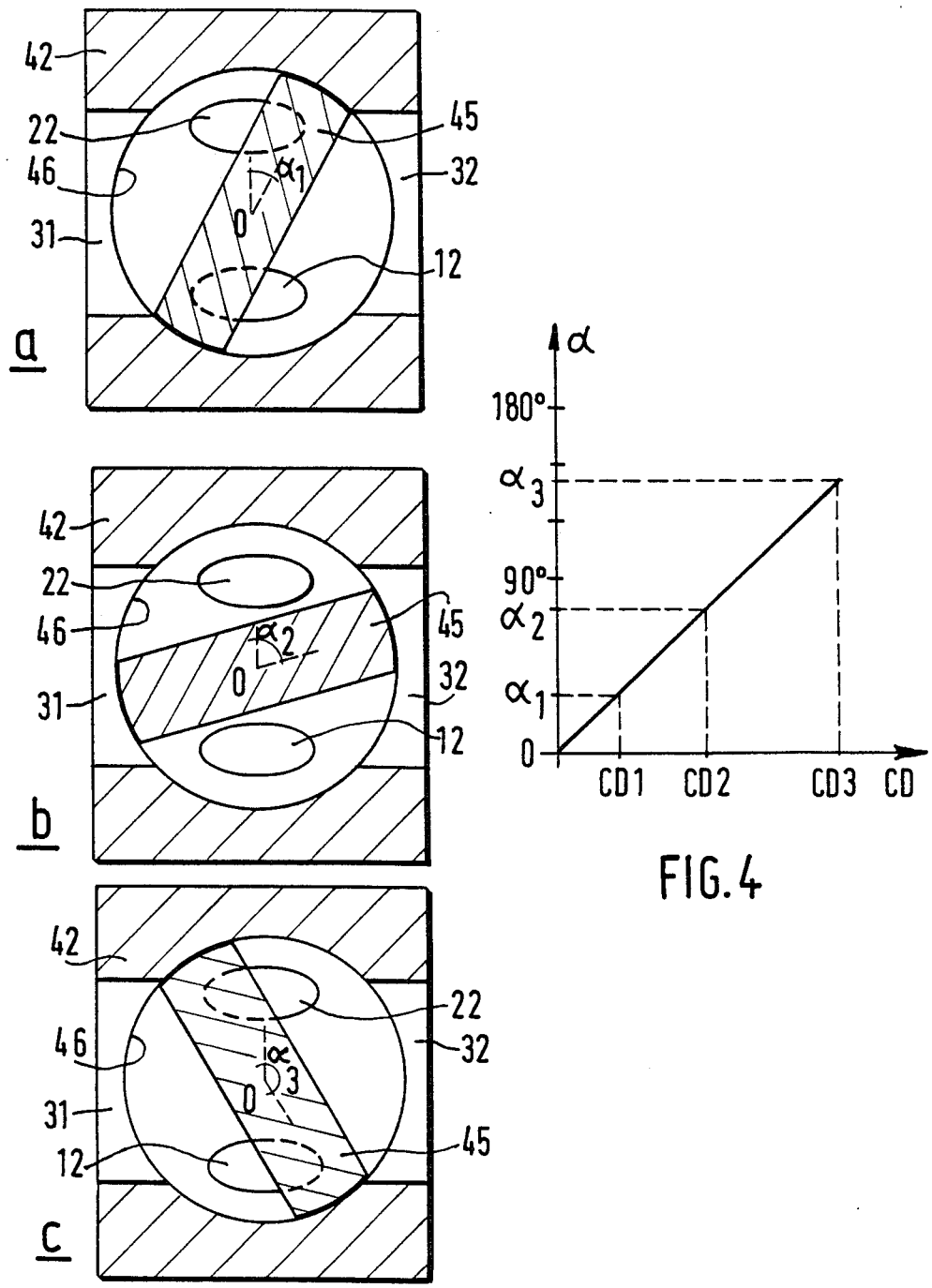
FIG. 2 shows a sectional view of the rotary distributor of the system of FIG. 1, for three different positions of its rotating piece.
FIG. 4 shows the angular position of the rotary piece of the rotary distributor of FIG. 2 as a function of a control voltage.

FIG. 2, which is a sectional view perpendicular to axis 44 of body 42 of distributor 4 shows that this latter has a recess 46, inside which moves a rotary piece 45, driven by the motor 41. The recess 46 is here a cylindrical volume with circular base and center O where the axis 44 of FIG. 1 is projected. Four orifices 12, 22, 31 and 32 formed in the walls of recess 46 communicate with ducts 14, 24, 34 and 43 respectively, that is to say with bag 1, reservoir 2, the inlet and outlet of pump 3, respectively. The orifices 31 and 32 are formed in the cylindrical wall of recess 46, symmetrical with respect to each other relatively to the axis 44 and here symmetrical with respect to the horizontal plane, in FIG. 2, passing through the axis 44. The orifices 12 and 22 are formed in one of the circular bases of recess 46. They are symmetrical with each other relatively to the axis 44 and here symmetrical with respect to the vertical plane, in FIG. 2, passing through the axis 44. They have substantially the shape of an ellipsis with large horizontal axis, in FIG. 2. The rotary piece 45 is a thick rectangular plate mounted for movement about axis 44 so that its four edges mate sealingly with the walls of recess 46.

The thickness of the rotary piece 45 is slightly less, here, than the large axis of the elliptic orifices 12 and 22, and more particularly less than the dimension of orifices 31 and 32 in the plane of FIG. 2.

Thus, if we call the angle between the vertical, in FIG. 2, and piece 45, angle $\alpha$, when $\alpha$ is close to the value $\alpha_1$, here equal to 30°, that is to say when piece 45 is in the position a of FIG. 2, orifices 31 and 22 communicate through the inner volume of recess 46, as moreover do the orifices 32 and 12. The position a corresponds then to inflation of the bag.

Similarly, when $\alpha$ is close to the value $\alpha_2$, here equal to 75°, which corresponds to the position b in FIG. 2, orifices 31 and 22 continue to communicate, as well as orifices 32 and 12, but, because orifices 31 and 32 communicate together, with the thickness of piece 45 being less than their dimension, the bag 1 and reservoir 2 are placed in direct communication not passing through pump 3. The position b may then correspond to the situation in which bag 1 empties itself into reservor 2, if, of course, the pressure in bag 1 is greater than the pressure in reservoir 2. When angle $\alpha$ decreases from the value $\alpha_2$, there is progressive closure of the smallest section in each path of the air between bag 1 and reservoir 2, that is to say of the sections of the parts of orifices 31 and 32 in communication with orifices 12 and 22, respectively. When $\alpha$ reaches a lower limit value, here equal to 60°, direct communication between bag 1 and reservoir 2 is cut off. On the other hand, when $\alpha$ increases from the value $\alpha_2$, the preceding sections increase and become maximum for $\alpha=90°$. Thus, we may say that, when motor 44 controls piece 45 so that $\alpha$ varies from 60° to 90°, the distributor 4 places bag 1 and reservoir 2 directly and progressively in communication. In fact, for $\alpha=60°$ this communication is cut off, for $\alpha$ between 60° and 90°, the smallest section in the path of the air increase as a function of $\alpha$, these sections being maximum for $\alpha=90°$.

Similarly, when $\alpha$ is close to the value $\alpha_3$, here equal to 143°5, which corresponds to position c in FIG. 2, the orifices 31 and 12 communicate through the inner volume of recess 46, as moreover do the orifices 32 and 22. The position c corresponds then to deflation of bag 1 by pump 3. When the angle $\alpha$ increases from the value $\alpha_3$, there is progressive closure of orifices 12 and 22 and when $\alpha$ reaches a limit value, here equal to 167°, the sections in the path of the air between the inlet of pump 3 and bag 1, as well as between the outlet of pump 3 and the reservoir 2, are minimum. The rotary piece 45 must not theoretically be controlled so that $\alpha$ becomes greater than $\alpha_3$, but if that occurs following a false maneuver, orifices 12 and 22 each communicate at one and the same time with orifices 31 and 32, so that pump 3 is never in the situation where its inlet and its outlet are blocked. When $\alpha$ decreases from $\alpha_3$; the sections in the path of the air between the inlet of pump 3 and bag 1, as well as between the outlet of pump 3 and reservoir 2, increase and become maximum for $\alpha=120°$. Thus, we may say that, when motor 44 controls piece 45 so that $\alpha$ varies from 167° to 120°, the distributor 4 places reservoir 2 and bag 1 progressively in communication through pump 3.

The electronic circuit 5 will now be described with reference to FIG. 3. In a way known per se, it comprises an electric energy source for supplying its different components with power, and is not shown in the FIG., for the sake of simplicity. The electronic circuit comprises first of all a reference signal generator 51, having two analog outputs delivering respectively a pressure reference signal CP and a coarse reference signal CG for distributor 4. The reference signal generator 51 is also provided with two binary outputs delivering respectively an inflation-deflation reference signal GD and a reference signal DP for deflation by the pump.

An analog subtractor 52 receives at its plus input the signal CP and at its minus input, connected to connection 511, an analog signal P. The output of subtractor 52 is connected to the input of a first controllable switch 53 with two outputs, the control input of which receives the binary signal GD. The first output of switch 53 is connected to the input of a circuit 54 controlling the motors 31, which circuit has two outputs connected to connection 531, through a double switch 61, with a control input receiving the signal GD. The second output of switch 53 is connected to the input of a second controllable switch 55, with two outputs, whose control input receives the binary signal DP.

The first output of switch 55 is connected through an inverting amplifier 56 to a first input of a third controllable switch 58, with two inputs and one output, the control input of which receives the binary signal DP. The second output of switch 55 is connected to the second input of switch 58, through a non inverting amplifier 57.

The output of switch 58 is connected to a first input of an analog adder 59, whose second input receives the signal CG and whose output delivers a signal CD to the input of a circuit 60 controlling motor 41, whose output is connected to the connection 541.

The reference signal generator 51 is adapted so as to produce the four periodic signals CP, CG, GD and DP of period T, shown in FIG. 5 which will be described in further detail subsequently. The design of such a circuit is within the scope of a man skilled in the art and will not be described further here.

Circuit 54 is adapted for supplying motors 31 with power so that their speed is an increasing function of the analog voltage applied to its input. Its design is then within the scope of a man skilled in the art.

Circuit 60 is of known type which controls motor 41, here a stepper motor, so that the position of the rotary piece 45 of the distributor, defined by the angle $\alpha$ of FIG. 2, varies as a function of the signal CD applied to its input in accordance with a law, here linear, represented in FIG. 4, where the values CD1, CD2 and CD3 of the signal CD correspond to the above defined angles $\alpha_1$, $\alpha_2$ and $\alpha_3$. The design of circuits 60 is also within the scope of a man skilled in the art.

The system which has just been described operates as follows. The pressure reference signal CP follows a predetermined law which may be chosen arbitrarily and which, in practice, is chosen so that the artificial heart controlled simulates as well as possible the operation of a real heart. FIG. 5 shows a typical trend for a cycle of duration T, which cycle may be divided into three phases, in the frequent case where the pressure in the reservoir is equal to the atmospheric pressure $P_{atm}$.

The first phase corresponds to the inflation phase of bag 1. During this phase, the reference pressure increases, from the value $P_{atm}$ and as far as a maximum value $P_{max}$. During the inflation phase, signal CG assumes the value CD1 and the signals GD and DP remain at the logic level O.

The second phase corresponds to the initial deflation phase, during which the reference pressure decreases, while remaining greater than the atmospheric pressure $P_{atm}$. During this initial deflation phase, the signal CG assumes the value CD2, signal GD is at logic level 1, and signal DP is at logic level O.

The third phase corresponds to the final deflation phase, during which the reference pressure becomes less than the atmospheric pressure $P_{atm}$ and here levels out at a minimum pressure $P_{min}$. During this final deflation phase, the signal CG assumes the value CD3, and signals GD and DP remain at logic level 1.

The cycle which has just been described is then repeated, identical to itself.

During the first (inflation) phase the output of subtractor 52, which then represents the difference between the reference pressure and the pressure P measured by sensor 11, is applied by switch 53 controlled by signal GD at level O to the input of circuit 54. Since no signal is then applied to the input of switch 55, the signal CD is equal to the signal CG, that is to say to the value CD1 which causes the rotary piece to remain motionless in the position a of FIG. 2, that is to say in the inflation position. In this position, the error, that is to say the difference between the reference pressure and the measured pressure P, controls the speed of motors 31, which reacts in its turn on the pressure in the bag, and circuit 54 is adapted so that the servo loop thus formed permanently ensures equality of pressure P and the reference pressure.

During the initial, as during the final, deflation phase, motors 31 are no longer supplied with power, since the double switch 61 is open, signal GD being at level 1. Nevertheless, because of its inertia and that of motors 31, pump 33 continues to rotate during the whole deflation, whose duration is generally fairly short, of the order of a second.

During the initial deflation phase, the error signal at the output of subtractor 52 is applied through the inverting amplifier 56 to adder 59 and signal CD then represents the sum of the coarse reference signal CG of the distributor, at that time equal to CD2, and of the amplified error signal. With the gain of amplifier 56 suitably adjusted, signal CD deviates all the more from the values CD2 the higher the error signal. That results in moving the rotary piece 45 about the position b in FIG. 2, i.e. the progressive control for placing bag 1 and reservoir 2 in direct communication, which in its turn reacts on the pressure, and the amplifier 56 is adjusted so that the servo loop thus formed permanently ensures equality of the pressure P and the reference pressure.

During the final deflation phase, the inverting amplifier 56 is replaced by the non inverting amplifier 57 and the coarse reference signal CG of the distributor assumes the value CD3, which results in moving the rotary piece 45 about the position c in FIG. 2. Then the pump 3, which is still rotating because of its inertia, is used for emptying bag into reservoir 3, the progressive control of the rotary piece 45 about its position c being controlled, as before in the initial deflation phase, so as to permanently ensure equality of pressure P and the reference pressure.

Naturally, the invention is not limited to the description which has just been made thereof. Thus, and in particular in the case where the desired deflation time is too long, and the pressure $P_{min}$ to low for pump 3 to be able to maintain it in bag 1 by using the inertia alone, it would be within the scope of a man skilled in the art to alter the preceding arrangement so as to supply again motors 31 with power at the end of deflation.

Similarly, it may not be necessary to control the rotary piece 45 during the whole deflation time and, for example, during the initial above defined deflation phase, the preceding arrangement being adapted so that bag 1 empties itself directly and freely into reservoir 2.

It is not necessary to use a gear displacement pump driven by two motors and any other pump may be suitable provided that it has a certain inertia, which is generally the case.

Naturally, the representation shown in FIG. 1 is schematical. In particular, in the case of an implanted system, reservoir 2 is not external to the system, as in this FIG., but itself contains the system, for which it serves as housing.

What is claimed is:

1. A system for inflating and deflating at least one inflatable bag comprising:

at least one inflatable bag;
a reservoir containing an inflation fluid;
at least one pump having an inlet an outlet and at least one means which moves in a predetermined direction, for moving a fluid from said inlet to said outlet;
means for driving said pump to move said moving means;
a controllable means for supplying operating power to said driving means causing it to drive said pump;
a controllable communicating means for selectively providing fluid communication paths among said reservoir, bag and pump; and
control means for controlling said power supply means and said communications means;
said control means operating during a period of bag inflation to control said communication means to provide a fluid communication path between said reservoir and pump inlet and a fluid communication path between said bag and pump outlet and to control said power supply means to supply power to said driving means so that the pressure of fliud in the bag is at all times equal to a reference pressure which varies with time according to a first predetermined law;
said control means operating during a period of bag deflation to turn off said power supply means and, at least during a final deflation phase, to control said communication means to provide a fluid communication path between said bag and said pump inlet and a fluid communication path between said reservoir and said pump outlet, said pump moving means moving by inertia, during deflation, in said predetermined direction to drive fluid from said bag to said reservoir.

2. The system as claimed in claim 1, wherein, said control means controls said communication means during deflation to place the reservoir and the bag progressively in fluid communication through the pump so as to empty the bag into the reservoir and cause the pressure of the fluid in the bag to evolve so that it is equal at all times to a reference pressure in accordance with a second predetermined law.

3. The system as claimed in claim 1, wherein, said control means controls said communication means during deflation to place the reservoir and the bag directly in communication so that the bag begins to empty itself directly into the reservoir and then controls said communication means so that the pump continues to empty the bag into the reservoir.

4. The system as claimed in claim 1, wherein, said control means controls said communication means during deflation to place the reservoir and the bag directly and progressively in communication so that the bag begins to empty itself directly into the reservoir, and so that the pressure of the fluid in the bag evolves so that at all times it is equal to a reference pressure in accordance with a second predetermined law, and then said control means controls said communication means so that the pump continues to empty the bag into the reservoir.

5. The system as claimed in claim 1, wherein a sensor is provided for measuring the pressure in the bag, said control means being connected to the sensor and comparing the pressure measured by the sensor with said reference pressure and progressively controlling the power supply means during inflation and the communication means during deflation.

6. The system as claimed in claim 1, wherein said communication means includes a rotary distributor, whose body has an inner volume provided with four orifices communicating/respectively with the bag, the reservoir, the inlet and the outlet of the pump, a rotary piece inside said volume driven by a motor causing progressive establishment or interruption of communication between said orifices.

7. The system as claimed in claim 1, wherein said pump is a gear displacement pump and said means for moving comprises two gears, and the means for driving the pump comprise a motor for each of the gears.

8. The system as claimed in claim 2, wherein said control means controls said communication means during deflation to place the reservoir and the bag directly in communication, so that the bag begins to empty itself directly into the reservoir and then controls said communication means so that the pump continues to empty the bag into the reservoir.

9. The system as claimed in claim 2, wherein, said control means controls said communication means during deflation to place the reservoir and the bag directly and progressively in communication, so that the bag begins to empty itself directly into the reservoir, and so that the pressure of the fluid in the bag evolves so that at all times it is equal to a reference pressure in accordance with said second predetermined law, and then said control means controls said communications means so that the pump continues to empty the bag into the reservoir.

10. The system as claimed in claim 2, wherein a sensor is provided for measuring the pressure in the bag, said control means being connected to the sensor and comparing the pressure measured by the sensor with said reference pressure and progressively controlling the power supply means during inflation and the communication means during deflation.

11. The system as claimed in claim 3, wherein, said control means controls said communication means during deflation to place the reservoir and the bag directly and progressively in communication, so that the bag begins to empty itself directly into the reservoir and so that the pressure of the fluid in the bag evolves so that at all times it is equal to a reference pressure in accordance with a second predetermined law, and then said control means controls said communication means so that the pump continues to empty the bag into the reservoir.

12. The system as claimed in claim 3, wherein a sensor is provided for measuring the pressure in the bag, said control means being connected to the sensor for comparing the pressure measured by the sensor with said reference pressure and progressively controlling the power supply means during inflation and the communication means during deflation.

13. The system as claimed in claim 4, wherein a sensor is provided for measuring the pressure in the bag, said control means being connected to the sensor for comparing the pressure measured by the sensor with said reference pressure and progressively controlling the power supply means during inflation and the communication means during deflation.

14. The system as claimed in claim 8, wherein, said control means controls said communication means during deflation to place the reservoir and the bag directly and progressively in communication, so that the bag begins to empty itself directly into the reservoir and so that the pressure of the fluid in the bag evolves so that at all times it is equal to a reference pressure in accordance with said second predetermined law, and then said control means controls said communication means so that the pump continues to empty the bag into the reservoir.

* * * * *